United States Patent [19]

Bicker et al.

[11] Patent Number: 4,644,057
[45] Date of Patent: Feb. 17, 1987

[54] PROCESS FOR THE CLEAVAGE OF PEPTIDES AND PROTEINS AT THE METHIONYL BOND USING CYANOGEN CHLORIDE

[75] Inventors: Richard Bicker, Liederbach; Gerhard Seipke, Wiesbaden, both of Fed. Rep. of Germany

[73] Assignee: Hoechst Aktiengesellschaft, Fed. Rep. of Germany

[21] Appl. No.: 795,920

[22] Filed: Nov. 7, 1985

[30] Foreign Application Priority Data

Nov. 9, 1984 [DE] Fed. Rep. of Germany ....... 3440988

[51] Int. Cl.[4] .................... C07K 17/00; C12N 9/99; C12N 11/02
[52] U.S. Cl. .................... 530/409; 435/176; 435/177; 435/207; 530/345; 530/812
[58] Field of Search ........ 260/112 R, 112 B, 112.5 R; 435/176, 177, 207; 530/409, 345, 812

[56] References Cited

U.S. PATENT DOCUMENTS

| | | | |
|---|---|---|---|
| 3,645,852 | 2/1972 | Axen et al. ................ | 260/112 R X |
| 3,876,501 | 4/1975 | Hanushewsky ............ | 260/112 R X |
| 3,919,049 | 11/1975 | Kiuchi et al. .......................... | 435/207 |
| 3,935,072 | 1/1976 | Chibata et al. ............. | 260/112 R X |
| 4,496,689 | 1/1985 | Mitra ........................... | 260/112 B X |

OTHER PUBLICATIONS

Biochem. J. 48, 271–276 (1950), Aldridge.
Methods in Enzymology, vol. XI, 238–255, (1967), Gross.
J. Biol. Chem. 258(1983), 14354–14358, Fowler et al.
Document A: (Gross et al., "Selective Cleavage of the Methionyl Peptides in Ribonuclease with Cyanogen Bromide," The Journal of the American Chemical Society, vol. 83, pp. 1510–1511 (1961)).
Document B: (Ullmanns Encyklopadie Der Technischen Chemie, 4th Ed., vol. 9, p. 6568).
Document C: (Hoben–Weyl, "1. Qualitativer Nachweis," Methoden Der Organischen Chemie, vol. II, p. 545 (1953)).

*Primary Examiner*—Howard E. Schain
*Attorney, Agent, or Firm*—Finnegan, Henderson, Farabow, Garrett & Dunner

[57] ABSTRACT

The invention relates to a process for the cleavage of peptides and proteins at the methionyl bond using cyanogen chloride.

10 Claims, No Drawings

PROCESS FOR THE CLEAVAGE OF PEPTIDES AND PROTEINS AT THE METHIONYL BOND USING CYANOGEN CHLORIDE

Within the framework of the obtaining of peptides and proteins by genetic engineering (for example insulin, proinsulin, preproinsulin and its analogs, interferon, growth hormone), it has frequently proved advantageous initially to isolate the products in the form of "fusion proteins" of higher molecular weight.

The fusion proteins thus produced are more stable than the desired products and can, by utilization of induction systems, be isolated in higher yields. Suitable in principle for fusions of this type are all proteins which are synthesized in relatively large amounts by the host organisms, especially when their synthesis is readily inducible; there have been frequent descriptions of $\beta$-galactosidase, $\beta$-lactamase, parts of the Cro protein, of the $C_{II}$ protein and of the enzymes of tryptophan metabolism (especially Trp D and Trp E). Fusions of the desired gene product with $\beta$-galactosidase are particularly popular for this purpose, because the proteins which are initially produced in this are frequently sparingly soluble and thus easy to enrich (A. V. Fowler and I. Zabin, J. Biol. Chem. 258 (1983) 14354–58).

The desired products can be eliminated from the resulting fusion proteins using chemical and enzymatic methods, it being necessary that these cleavage reactions are highly specific in order to avert damage to the products.

Chemical methods of protein cleavage are usually referred to in connexion with peptide-sequence analysis of proteins (see, for example, Handbook of Protein Sequence Analyses, 2nd Edition, L. R. Croft, John Wiley and Sons; B. Witkop, Advan. Prot. Chem. 16 (1961), 221, and E. Gross, Methods in Enzymology, Vol. XI, 238 (1967)).

Reference is particularly frequently made to cleavage at methionyl bonds using cyanogen bromide (B. Witkop, Adv. Prot. Chem. 16 (1961) 221), since in general this achieves high cleavage yields without damage to other peptide bonds or amino acid side-chains.

In order to achieve high cleavage yields, use is normally made of large excesses of cyanogen bromide (up to 250 x; see the article by B. Witkop) relative to the methionyl bond which is to be cleaved, and of long reaction times, up to 30 hours, and room temperature. The reaction is carried out in a strongly acid medium, a preferred solvent being formic acid in the concentration range 70–88% by volume.

Cyanogen bromide (BrCN) is a solid (melting point 52° C., boiling point 62° C.), and a highly toxic compound. The lethal dose for a normal person is 92 ppm at an exposure time of 10 minutes (Gmelin Syst. No. 14 C, F 1. D 3 1976, pages 217–241; Petty's Industrial Hygiene and Toxicology, 3rd Edition, Vol. 2 c, page 4861). Spontaneous explosion of packages containing impure products has been described (see the brochure "Safety with Merck", E. Merck, Darmstadt 5/13090/60/1282 R).

Hence there are great problems with the manipulation of large amounts of BrCN in protein cleavage on the large industrial scale, and technical factors (for example conveyance of solids) play a part in addition to the safety aspects.

It has now been found, surprisingly, that it is possible to cleave the methionyl bond with cyanogen chloride (ClCN).

Thus the invention relates to a process for the cleavage of peptides and proteins at the methionyl bond, which comprises carrying out the cleavage with cyanogen chloride.

Protein cleavages using ClCN are not described in the literature.

The use of ClCN for non-enzymatic protein cleavage is not necessarily predictable to those skilled in the art, since the chemical reactivity of ClCN is strikingly different from that of BrCN (cf. in this context, Houben-Weyl, Vol. II, page 545; Ullmann Vol. 9, page 668, B. S. Thyagarajan, The Chemistry of Cyanogen Halides 2, (1968); R. T. Parfitt, J. Chem. Soc. (C), 140, (1967)). In addition to the differences in the reactivity and activity of BrCN and ClCN, differences have also been found in the way they react with identical reactants.

ClCN is a gas at room temperature (melting point $-6.9°$ C.; boiling point 13.0° C.); it is not as toxic as BrCN (cf. Gmelin Syst. No. 14 C, F 1, D 3, 1976, page 185; Petty's Industrial Hygiene and Toxicology, 3rd Edition, 1982, Vol. 2 c, page 4859). The lethal dose for humans is 159 ppm at an exposure time of 10 minutes (cf. 92 ppm for BrCN). Since the irritation threshold for ClCN is 2.5 mg/m$^3$, which is markedly lower than that of BrCN (6.0 mg/m$^3$), the "automatic warning" provided by ClCN is more evident. Thus it possesses considerable safety advantages for industrial use.

In addition, the use of ClCN also offers considerable advantages in processing technology: ClCN, being a gas, is more straightforward and hazard-free to meter and convey than is the solid BrCN.

When the reaction is complete, the excess cyanogen chloride can be removed from the reaction mixture by blowing in a suitable gas. Inert gases such as, for example, nitrogen are suitable. Suitable defoaming agents can be added to suppress the formation of foam. Examples which are very suitable are Wacker Chemie types SE 3, 6 and 9. Thereafter the reaction mixture is worked up in a customary manner.

The stream of gas loaded with ClCN can be passed through a washer which contains aqueous NaOH and-/or NaOCl solution. This results in the ClCN being broken down to give NaCl and NaOCN (see Gmelin Syst. No. 14 C, F 1, D 3, 1976, page 184; Petty's Industrial Hygiene and Toxicology, 3rd Edition 1982, Vol. 2 c, page 4859).

Using this procedure it is possible to dispose of the cleavage reagent (ClCN) considerably more safely than the more toxic BrCN. This entails the disposal being separate in time and space from the protein isolation, which can be carried out by known methods (evaporation, freeze-drying).

Cyanogen chloride is advantageously used in a 2 to 30-fold molar excess per methionyl bond which is to be cleaved. A 5 to 8-fold molar excess is preferred. The reaction time is usually 1–10 hours, preferably 3–6 hours.

A suitable reaction medium is a mixture of water and a mineral acid or an organic acid which is miscible with water. Organic acids are preferred, such as, for example, formic acid. The content of formic acid in the reaction medium can be 50–95% by volume, preferably 65–88% by volume.

The examples which follow are used to illustrate the invention but without restricting it to these.

EXAMPLE 1 (COMPARISON EXAMPLE)

1 g of β-Galactosidase from E. coli (content about 70%, methionine content 0.16 mmol/g determined by amino acid analysis) is stirred into 7.5 ml of 70% by volume HCOOH, and 0.135 g of cyanogen bromide (=1.28 mmol) is added.

The reaction mixture is stirred at room temperature for 6 hours, diluted with 100 ml of $H_2O$ and freeze-dried.

The residue amounts to 0.97 g of cleaved protein mixture.

β-Galactosidase is no longer detectable by gel electrophoresis (SDS-PAGE). It is found that the preferred molecular weight range for the protein fragments is 5,000–20,000 Dalton. According to amino acid analysis and methyl thiocyanate determination by gas chromatography, 94% cleavage has taken place.

EXAMPLE 2

1 g of β-Galactosidase from E. coli (content about 70%, methionine content 0.16 mmol/g determined by amino acid analysis) is stirred into 7.5 ml of a 70% by volume HCOOH, and 0.079 g of ClCN (=1.28 mmol) is added.

The reaction mixture is stirred at room temperature for 6 hours.

After reaction is complete, 1–5 μl of defoaming agent (SE 9 supplied by Wacker Chemie, Burghausen) are added and the excess cyanogen chloride is removed in about 1.5 hours by blowing in $N_2$ (15 l/h). The $N_2$ stream loaded with cyanogen chloride is passed into a wash bottle containing sodium hydroxide solution.

After the ClCN has been driven out, the solution is diluted with 100 ml of $H_2O$ and is freeze-dried. The residue amounts to 1 g.

β-Galactosidase is no longer detectable by SDS-PAGE. It is found that the preferred molecular weight range for the protein fragments is 5,000–20,000 Dalton. According to amino acid analysis and methyl thiocyanate determination by gas chromatography, 93% cleavage has taken place.

EXAMPLE 3

1 g of β-Lactamase, isolated from E. coli cells which contain the plasmid pBR 322 (content about 75%, methionine content 0.28 mmol/g) is stirred into 10 ml of 70% by volume HCOOH, and 0.236 g of ClCN (=2.28 mmol) is added.

The reaction mixture is stirred at room temperature for 6 hours.

After reaction is complete, 1–5 μl of defoaming agent (SE 9 supplied by Wacker Chemie, Burghausen) are added, and the excess cyanogen chloride is removed in about 1.5 hours by blowing in $N_2$ (15 l/h). The $N_2$ stream loaded with cyanogen chloride is passed into a wash bottle containing sodium hydroxide solution.

After the ClCN has been driven out, the solution is diluted with 100 ml of $H_2O$ and is freeze-dried.

The residue amounts to 0.99 g.

β-Lactamase is no longer detectable by SDS-PAGE. It is found that the principal molecular weight range for the protein fragments is 3,000–10,000 Dalton. According to amino acid analysis and methyl thiocyanate determination by gas chromatography, 92% cleavage has taken place.

We claim:

1. A process for the cleavage of peptides and proteins at the methionyl bond, which comprises carrying out the cleavage with cyanogen chloride.

2. The process as claimed in claim 1, wherein the excess cyanogen chloride is removed, after the reaction is complete, from the reaction mixture using a suitable gas, and the reaction mixture is then worked up in a customary manner.

3. The process as claimed in claim 2, wherein the excess cyanogen chloride is removed from the reaction mixture using nitrogen.

4. The process as claimed in claim 1, wherein cyanogen chloride is used in a 2 to 30-fold molar excess per methionyl bond which is to be cleaved.

5. The process as claimed in claim 1, wherein cyanogen chloride is used in a 5 to 8-fold molar excess per methionyl bond which is to be cleaved.

6. The process as claimed in claim 1, wherein the reaction is carried out in 1–10 hours.

7. The process as claimed in claim 3, wherein the reaction is carried out in 3–6 hours.

8. The process as claimed in claim 3, wherein the reaction medium used is a mixture of water and an acid which is miscible with water.

9. The process as claimed in claim 8, wherein the reaction medium used is a mixture of water and formic acid.

10. The process as claimed in claim 9, wherein the formic acid content in the reaction medium is 50–95% by volume.

* * * * *